(12) United States Patent
McIntosh

(10) Patent No.: US 9,408,876 B2
(45) Date of Patent: *Aug. 9, 2016

(54) LIVER STROMAL CELLS FOR PREVENTION AND TREATMENT OF IMMUNE RESPONSES IN TRANSPLANTATION

(75) Inventor: Kevin R. McIntosh, Ellicott City, MD (US)

(73) Assignee: Cognate Therapeutics, Inc., Sunnyvale, CA (US)

( * ) Notice: Subject to any disclaimer, the term of this patent is extended or adjusted under 35 U.S.C. 154(b) by 1761 days.

This patent is subject to a terminal disclaimer.

(21) Appl. No.: 11/222,316

(22) Filed: Sep. 8, 2005

(65) Prior Publication Data

US 2006/0057125 A1  Mar. 16, 2006

Related U.S. Application Data

(60) Provisional application No. 60/609,077, filed on Sep. 10, 2004.

(51) Int. Cl.

| A61K 35/407 | (2015.01) |
|---|---|
| A61K 39/00 | (2006.01) |
| C12N 5/071 | (2010.01) |
| A61K 35/12 | (2015.01) |

(52) U.S. Cl.
CPC ............ *A61K 35/407* (2013.01); *A61K 39/001* (2013.01); *C12N 5/067* (2013.01); *A61K 2035/122* (2013.01)

(58) Field of Classification Search
CPC ........................ A61K 35/407; A61K 39/001
USPC ........................................................ 424/93.7
See application file for complete search history.

(56) References Cited

U.S. PATENT DOCUMENTS 6,296,846 B1 * 10/2001 Sachs et al. ................. 424/93.21
6,328,960 B1    12/2001 McIntosh et al.

FOREIGN PATENT DOCUMENTS

| WO | WO96/23058 | * | 8/1996 | ............. A01N 63/00 |
|---|---|---|---|---|
| WO | WO 99/47163 | | 9/1999 | |
| WO | WO01/26470 | * | 4/2001 | ............. A01N 63/00 |

OTHER PUBLICATIONS

Bishop et al, Spontaneous acceptance of liver transplants in rodent: Evidence that liver leucocytes induce recipient T-cell death by neglect, Immunology and Cell Biology, 2002, vol. 80, p. 93-100.*
Kim, et al., The Role of Fas Ligand and Transforming Growth Factor Beta in Tumor Progression, *Cancer*, Jun. 1, 2004, vol. 100, p. 2281-2291, especially p. 2282.
Walczak, et al., The CD95 (APO-1/Fas) and the TRAIL (APO-2L) Apoptosis Systems, *Experimental Cell Research*, 256, 58-66 (2000).
Fan, et al., Successful Allogeneic Bone Marrow Transplantation (BMT) by Injection of Bone Marrow Cells via Portal Vein: Stromal Cells as BMT-Facilitating Cells, *Stem Cells*, 2001, vol. 19, p. 144-150.
Moore, et al., In Vitro Maintenane of Highly Purified, Transplantable Hematopoietic Stem Cells, *Blood*, 1997, vol. 89, p. 4337-4347.
Di Nicola et al., "Human bone marrow stromal cells suppress T-lymphocyte proliferation induced by cellular or non-specific mitgenic stimuli," *Blood* 99:3838-3843 (2002).
Le Blanc et al., "Mesenchymal Stem Cells Inhibit and Stimulate Mixed Lymphocyte Cultures and Mitogenic Responses Independently of the Major Histocompatibility Complex," *Scandinavian Journal of Immunology* 57:11-20 (2003).
Sigal et al., "The liver as a stem cell and lineage system," *Amer. J. Physiol.* 263:G139-G148 (1992).
Tse et al., "Suppression of Allogeneic T-cell Proliferation by Human Marrow Stromal Cells: Implications in Transplantation," *Transplantation* 75:389-397 (2003).
Götherström et al., "Immunologic properties of human fetal mesenchymal stem cells," *American Journal of Obstetrics and Gynecology* 190:239-245, 2004.
Götherström et al., "Immunomodulatory effects of human foetal liver-derived mesenchymal stem cells," *Bone Marrow Transplantation* 32:265-272, 2003.
Le Blanc, K., "Immunomodulatory effects of fetal and adult mesenchymal stem cells," *Cytotherapy* 5(6):485-489, 2003.

\* cited by examiner

*Primary Examiner* — Taeyoon Kim
*Assistant Examiner* — Tiffany Gough
(74) *Attorney, Agent, or Firm* — DLA Piper LLP (US)

(57) ABSTRACT

The present invention encompasses methods and compositions for reducing an immune response to a transplant in a recipient by treating said recipient with an amount of liver stromal cells effective to reduce or inhibit host rejection of the transplant. Also disclosed is a method of inducing a reduced immune response against a host by foreign tissue, i.e., graft versus host disease, by treatment with liver stromal cells.

26 Claims, 3 Drawing Sheets

LIVER STROMAL CELLS FOR PREVENTION AND TREATMENT OF IMMUNE RESPONSES IN TRANSPLANTATION

CROSS-REFERENCE TO RELATED APPLICATIONS

This application claims priority under 35 U.S.C. §119(e) to U.S. Provisional Patent Application No. 60/609,077, filed Sep. 10, 2004, which is incorporated by reference herein in its entirety.

BACKGROUND OF THE INVENTION

The liver is a dynamic organ that plays an important role in a variety of physiological processes. The complex functions of the liver include metabolism, storage, excretion, secretion of plasma proteins such as albumin and detoxification of harmful substances by enzymes of the cytochrome P-450 system. In addition, the usually quiescent liver is also capable of remarkable mitotic activities under certain circumstances. The major cell population of the liver is the parenchymal cells (PC), also known as hepatocytes. The liver also contains several other cell types such as endothelial cells, adipocytes, fibroblastic cells and Kupffer cells. The ability of liver cells to undergo rapid regeneration, when the liver is damaged or partially removed, makes the liver a potential source of stem cells.

It is currently believed that the liver has a stem cell and lineage system which has several parallels to the gut, skin and hemopoietic systems (Sigal et al., 1993 Amer. J. Physiol., 263:139-148). As such, there are progenitor cell populations in the liver of animals of all ages. These cells when isolated from the liver may serve as potential candidates for cell therapy.

The mammalian immune system plays a central role in protecting individuals from infectious agents and preventing tumor growth. However, the same immune system can produce undesirable effects such as the rejection of cell, tissue and organ transplants from unrelated donors. The immune system does not distinguish beneficial intruders, such as a transplanted tissue, from those that are harmful, and thus the immune system rejects transplanted tissues or organs. Rejection of transplanted organs is generally mediated by alloreactive T cells present in the host which recognize donor alloantigens or xenoantigens.

Immunologic tolerance is an actively induced unresponsiveness to a specific antigen as the result of antigen-induced functional inactivation or death of lymphocytes that are specific for that antigen. Antigens that induce such tolerance are termed "tolerogens," so as to be distinguished from immunogens which are antigens that generate immune responses. One mechanism of B cell tolerance and failure to produce antibodies involves the interaction of antigens with specific B cells (the first step in B cell activation) in the absence of stimulation by helper T cells or other antigen presenting cells (the second step in B cell activation). Other mechanisms of B cell tolerance have been proposed. For example, B cells can become anergic due to a block in surface immunoglobulin-mediated signaling ("antigen-competition"), in the absence of T cells. Additionally, in the absence of co-stimulation by an antigen presenting cell, strong crosslinking of B cell surface immunoglobulins by an antigen can induce apoptotic death of normal, mature B cells, but may not induce apoptosis in B cells that produce autoimmune antibodies (Tsubata et al., 1994, Curr. Biol. 4:8-17).

T cell tolerance is achieved 1) in the thymus where thymocytes reactive for self-peptides are eliminated by clonal deletion (central tolerance), and 2) in the periphery by exposure to self-antigens under tolerogenic conditions (peripheral tolerance). Clonal deletion can also result from expression of cell death molecules on antigen presenting cells. Classic examples of cell death molecules are Fas ligand (FasL) and tumor necrosis factor-related apoptosis-inducing ligand (TRAIL ligand), which ligate their receptors, Fas and DR4, respectively, on activated T cells, inducing apoptosis of the T cells. The interaction of CD27, a member of the TNFR superfamily, and the CD27-ligand (CD70) also induces T cell apoptosis.

The transplantation of cells, tissues, and organs between genetically disparate individuals invariably is associated with risk of graft rejection. Nearly all cells express products of the major histocompatibility complex, MHC class I molecules. Further, many cell types can be induced to express MHC class II molecules when exposed to inflammatory cytokines. Additional immunogenic molecules include those derived from minor histocompatibility antigens such as Y chromosome antigens recognized by female recipients. Rejection of allografts is mediated primarily by T cells of both the CD4 and CD8 subclasses (Rosenberg et al., 1992 Annu. Rev. Immunol. 10:333). Alloreactive CD4 T cells produce cytokines that exacerbate the cytolytic CD8 response to alloantigen. Within these subclasses, competing subpopulations of cells develop after antigen stimulation that are characterized by the cytokines they produce. Th1 cells, which produce IL-2 and IFN-γ, are primarily involved in allograft rejection (Mossmann et al., 1989 Annu. Rev. Immunol. 7:145). Th2 cells, which produce IL-4 and IL-10, can down-regulate Th1 responses through IL-10 (Fiorentino et al. 1989 J. Exp. Med. 170:2081). Indeed, much effort has been expended to divert undesirable Th1 responses toward the Th2 pathway. Undesirable alloreactive T cell responses in patients (allograft rejection, graft-versus-host disease) are typically treated with immunosuppressive drugs such as prednisone, azathioprine, and cyclosporine A. Unfortunately, these drugs generally need to be administered for the life of the patient and they have a multitude of dangerous side effects including generalized immunosuppression.

A major goal in organ transplantation is the permanent engraftment of the donor organ without inducing a graft rejection immune response generated by the recipient, while preserving the immunocompetence of the recipient against other foreign antigens. Typically, in order to prevent host rejection responses, nonspecific immunosuppressive agents such as cyclosporine, methotrexate, steroids and FK506 are used. These agents must be administered on a daily basis and if administration is stopped, graft rejection usually results. However, a major problem in using nonspecific immunosuppressive agents is that they function by suppressing all aspects of the immune response, thereby greatly increasing a recipient's susceptibility to infection and other diseases, including cancer.

Furthermore, despite the use of immunosuppressive agents, graft rejection still remains a major source of morbidity and mortality in human organ transplantation. Most human transplants fail within 10 years without permanent graft acceptance. Only 50% of heart transplants survive 5 years and 20% of kidney transplants survive 10 years. (Opelz et al., 1981, Lancet 1:1223).

It is currently believed that a successful transplantation is dependent on the prevention and/or reduction of an unwanted immune response by a host to a transplant mediated by immune effector cells to avert host rejection of donor tissue.

Also advantageous for a successful transplantation is a method to eliminate or reduce an unwanted immune response by a donor tissue against a recipient tissue known as graft-versus-host disease. Thus, there is long-felt need for methods to suppress or otherwise prevent an unwanted immune response associated with transplantation of cells, tissues, and organs between genetically disparate individuals. The present invention meets this need.

BRIEF SUMMARY OF THE INVENTION

The invention includes a method of reducing an immune response to a transplant in a recipient by treating the recipient with an amount of liver stromal cells (LSCs) effective to reduce or inhibit host rejection of the transplant. The invention also includes a method of inducing a reduced immune response against a host by foreign tissue, i.e., graft versus host disease, by treatment with LSCs. The LSCs can be administered before, at the same time as, or after the transplant.

The invention also includes a method of treating a transplant recipient to reduce in the recipient an immune response of effector cells against an alloantigen to the effector cells comprising administering to a transplant recipient LSCs in an amount effective to reduce an immune response of effector cells against an alloantigen to the effector cells, whereby in the transplant recipient the effector cells have a reduced immune response against the alloantigen.

In one embodiment, the effector cell is a T cell.

In another embodiment, the T cell is from a donor and the alloantigen is from the recipient.

In another embodiment, the T cell is from a recipient and the alloantigen is from a donor.

In yet another embodiment, the T cell is present in the transplant.

In a further embodiment, the transplant is bone marrow.

In another embodiment, the transplant is a hematopoietic stem cell.

In one embodiment, the transplant is a neural stem cell.

In a further embodiment, the LSCs are expanded in culture prior to administering to a transplant recipient.

In another embodiment, the effector cells are T cells from a donor previously activated by contacting the T cells with a cell or a tissue from the recipient prior to transplantation in order to activate the T cells, and further wherein the immune response is the reactivation of the T cells.

In another embodiment, the LSCs are administered to the transplant recipient to treat rejection of the transplant by the recipient.

In yet another embodiment, the LSCs are human LSCs.

In one embodiment, the method further comprises administering to the recipient an immunosuppressive agent.

In one embodiment, the transplant is a solid organ. Preferably, the solid organ is selected from the group consisting of heart, pancreas, kidney, lung and liver.

In a further embodiment, the LSCs are administered intravenously to the recipient.

In another embodiment, the effector cells are cells of a recipient of the donor transplant.

In yet another embodiment, the LSCs are genetically modified.

The invention also includes a method for treating a transplant recipient to reduce in the recipient an immune response of effector cells against an alloantigen to the effector cells comprising transplanting to a transplant recipient a transplant treated with LSCs in an amount effective to reduce an immune response of effector cells against an alloantigen to the effector cells, whereby in the transplant recipient the effector cells have a reduced immune response against the alloantigen.

The invention also includes a method of reducing an immune response of effector cells against allogeneic cells comprising treating the effector cells with LSCs.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

DETAILED DESCRIPTION

Figure 1:
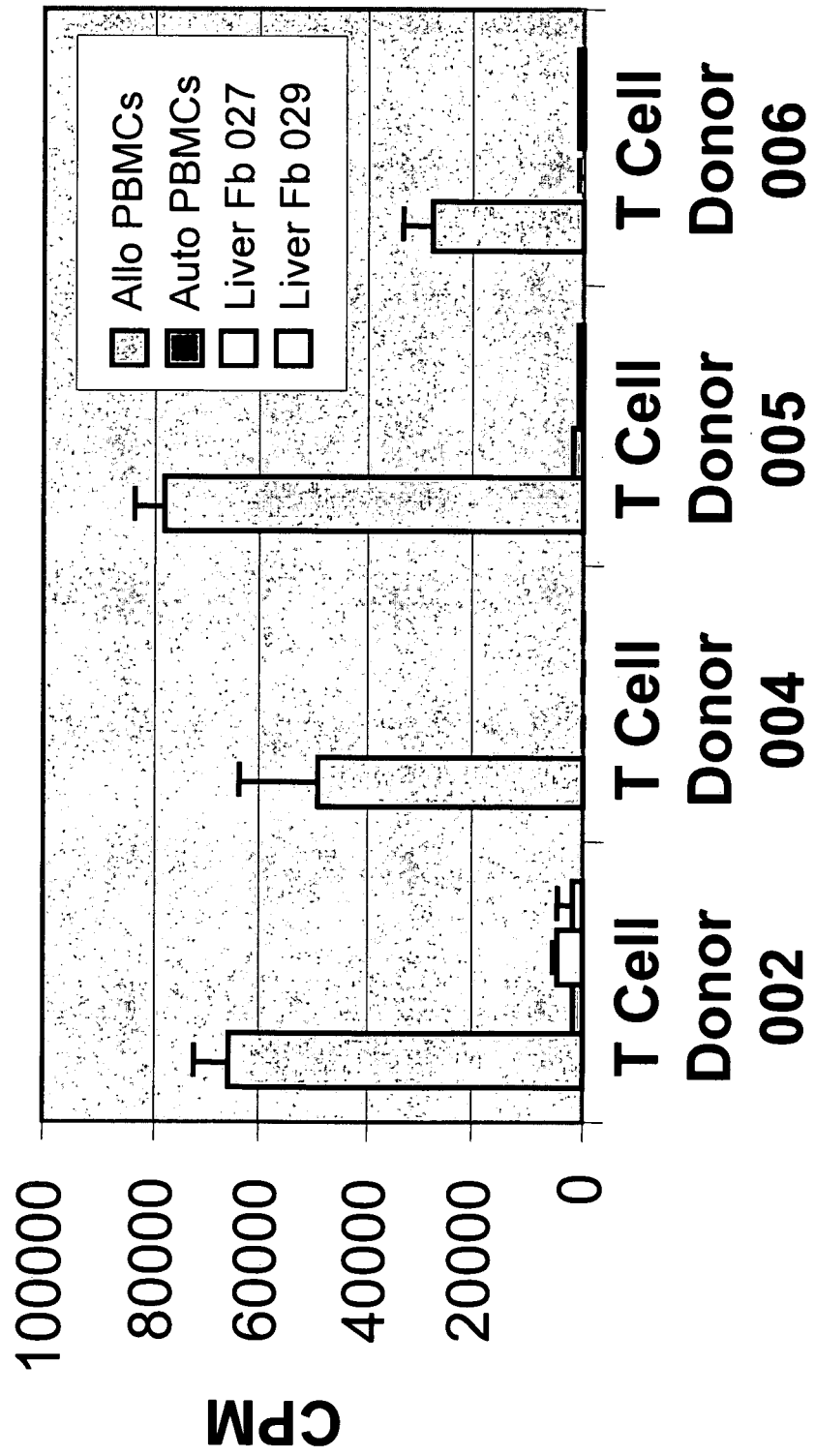
FIG. 1 is a graph depicting the immunogenicity of liver stromal cells (LSCs).

The present invention relates to the discovery that stromal cells from liver (LSCs) possess novel immunological characteristics and therefore can be useful in transplantation of a transplant, for example a biocompatible lattice or a donor tissue, organ or cell, by reducing and/or eliminating an immune response against the transplant by the recipient's own immune system. As described more fully below, LSCs play a role in inhibiting and/or preventing allograft rejection of a transplant.

In addition, the data disclosed herein also demonstrate that LSCs are useful in the inhibition and/or prevention of an unwanted immune response by a donor transplant, for example, a biocompatible lattice or a donor tissue, organ or cell, against a recipient tissue known as graft-versus-host disease.

Accordingly, the present invention encompasses methods and compositions for reducing and/or eliminating an immune response to a transplant in a recipient by treating the recipient with an amount of LSCs effective to reduce or inhibit host rejection of the transplant. Also encompassed are methods and compositions for reducing and/or eliminating an immune response in a host by the foreign transplant against the host, i.e., graft versus host disease, by treating the donor transplant and/or recipient of the transplant liver stromal cells in order to inhibit or reduce an adverse response by the donor transplant against the recipient.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the term "autologous" is meant to refer to any material derived from the same individual to which it is later to be re-introduced into the individual.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines, extracellular matrix material, etc.) that facilitate the development of appropriate tissue types and structures.

As used herein, the term "bone marrow stromal cells," "stromal cells," "mesenchymal stem cells" or "MSCs" are used interchangeably and refer to the small fraction of cells in bone marrow which can serve as stem cell-like precursors to osteocytes, chondrocytes, monocytes, and adipocytes. Bone marrow stromal cells have been studied extensively (Castro-Malaspina et al., 1980, Blood 56:289-30125; Piersma et al., 1985, Exp. Hematol 13:237-243; Simmons et al., 1991, Blood 78:55-62; Beresf ord et al., 1992, J. Cell. Sci. 102: 341-3 51; Liesveld et al., 1989, Blood 73:1794-1800; Liesveld et al., Exp. Hematol 19:63-70; Bennett et al., 1991, J. Cell. Sci. 99:131-139). Bone marrow stromal cells may be derived from any animal. In some embodiments, stromal cells are derived from primates, preferably humans.

As used herein, "liver stromal cell" or "LSC" refers to a small fraction of fibroblastic-type cells derived from liver. LSCs, when contacted with T cells from an individual that is not the same individual from which the LSCs were obtained, do not elicit a T cell response. In addition, LSCs are able to suppress alloreactive T cell proliferation during an immune response. For example, LSCs can suppress a mixed lymphocyte reaction (MLR) between allogeneic T cells and peripheral blood mononuclear cells (PBMCs).

"Neural stem cell" or "NSC" is used herein to refer to undifferentiated, multipotent, self-renewing neural cell. A neural stem cell is a clonogenic multipotent stem cell which is able to divide and, under appropriate conditions, has self-renewal capability and can terminally differentiate into neurons, astrocytes, and oligodendrocytes. Hence, the neural stem cell is "multipotent" because stem cell progeny have multiple differentiation pathways. A neural stem cell is capable of self maintenance, meaning that with each cell division, one daughter cell will also be, on average, a stem cell.

"Graft" refers to a cell, tissue, organ or otherwise any biological compatible lattice for transplantation.

"Allogeneic" refers to a graft derived from a different animal of the same species.

"Xenogeneic" refers to a graft derived from an animal of a different species.

"Transplant" refers to a biocompatible lattice or a donor tissue, organ or cell, to be transplanted. An example of a transplant may include but is not limited to skin, bone marrow, and solid organs such as heart, pancreas, kidney, lung and liver.

As defined herein, an "allogeneic liver stromal cell (LSC)" is obtained from a different individual of the same species as the recipient.

"Donor antigen" refers to an antigen expressed by the donor tissue to be transplanted into the recipient.

"Alloantigen" is an antigen that differs from an antigen expressed by the recipient.

As used herein, an "effector cell" refers to a cell which mediates an immune response against an antigen. In the situation where a transplant is introduced into a recipient, the effector cells can be the recipient's own cells which elicits an immune response against an antigen present in the donor transplant. In another situation, the effector cell can be part of the transplant, whereby the introduction of the transplant into a recipient results in the effector cells present in the transplant eliciting an immune response against the recipient of the transplant.

By the term "treating a transplant recipient to reduce in said recipient an immune response of effector cells against an alloantigen to the effector cells," as the phrase is used herein, is meant decreasing the endogenous immune response against the alloantigen in a recipient by any method, for example administering LSCs to a recipient, compared with the endogenous immune response in an otherwise identical animal which was not treated with LSCs. The decrease in endogenous immune response can be assessed using the methods disclosed herein or any other method for assessing endogenous immune response in an animal.

As used herein, the term "growth medium" is meant to refer to a culture medium that promotes growth of cells. A growth medium may contain animal serum but this is not always a required component in that the growth medium may also be serum free.

As used herein, the term "growth factor product" refers to a protein, peptide, mitogen, or other molecule having a growth, proliferative, differentiative, or trophic effect on a cell. For example, growth factor products useful in the treatment of CNS disorders include, but are not limited to, nerve growth factor (NGF), brain-derived neurotrophic factor (BDNF), the neurotrophins (NT-3, NT-4/NT-5), ciliary neurotrophic factor (CNTF), amphiregulin, FGF-1, FGF-2, EGF, TGFα, TGFβs, PDGF, IGFs, and the interleukins; IL-2, IL-12, IL-13.

"Immunophenotype" of a cell is used herein to refer to the phenotype of a cell in terms of the surface protein profile of a cell.

An "isolated cell" refers to a cell which has been separated from other components and/or cells which naturally accompany the isolated cell in a tissue or mammal.

As used herein, the term "modulate" is meant to refer to any change in biological state, i.e. increasing, decreasing, and the like.

As used herein, the term "non-immunogenic" is meant to refer to the discovery that LSCs do not induce proliferation of T cells in an MLR. However, the term non-immunogenic should not be limited to the absence of induction of T cell proliferation in an MLR, but rather should also be construed to apply to the absence of T cell proliferation in vivo following administration of LSCs to an animal.

"Proliferation" is used herein to refer to the reproduction or multiplication of cells. That is, proliferation encompasses production of a greater number of cells, and can be measured by, among other things, simply counting the numbers of cells, measuring incorporation of $^3$H-thymidine into the cell, and the like.

The term "stromal cell medium" as used herein, refers to a medium useful for culturing LSCs. A non-limiting example of a stromal cell medium is a medium comprising DMEM/F 12 Ham's, 10% fetal bovine serum, 100 U penicillin/100 µg streptomycin/0.25 µg Fungizone. Typically, the stromal cell medium comprises a base medium, serum and an antibiotic/antimycotic. However, LSCs can be cultured in a stromal cell medium without an antibiotic/antimycotic and supplemented with at least one growth factor. The preferred base medium is DMEM/F12 (1:1). The preferred serum is fetal bovine serum (FBS) but other sera may be used including horse serum or human serum. Preferably up to 20% FBS is added to the above media in order to support the growth of stromal cells. However, a defined medium can be used if the necessary growth factors, cytokines, and hormones in FBS for stromal cell growth are identified and provided at appropriate concentrations in the growth medium. It is further recognized that additional components may be added to the culture medium. Such components include but are not limited to antibiotics, antimycotics, albumin, growth factors, amino acids, and other components known in the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing stromal cells. Rather, any media capable of supporting stromal cells in tissue culture may be used.

As used herein, a "therapeutically effective amount" is the amount of LSCs which is sufficient to provide a beneficial effect to the subject to which the LSCs are administered.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

The term "genetic modification" as used herein refers to the stable or transient alteration of the genotype of an LSC by intentional introduction of exogenous DNA. Preferably, the exogenous DNA is an isolated nucleic acid. The DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

DESCRIPTION

The present invention relates to the discovery that when liver stromal cells (LSCs) are contacted with T cells obtained from a different individual (allogeneic T cells), the allogeneic T cells do not proliferate. Prior art dogma suggests that when T cells are mixed with any other cell, T cell proliferation ensues. This phenomenon is known as a mixed lymphocyte reaction (MLR). The data disclosed herein demonstrate that T cells derived from an individual are not responsive to LSCs obtained from a different individual. Therefore, based upon the disclosure herein, LSCs are not immunogenic to the immune system with respect to manifesting a T cell response.

In addition to the non-immunogenic phenotype of LSCs with respect to T lymphocytes in a different individual, the present invention also relates to the novel discovery that LSCs can suppress an MLR between allogeneic cells, for example between T cells from an individual and peripheral blood mononuclear cells (PBMCs) from another individual. These unexpected results demonstrate that LSCs can actively reduce the allogeneic T cell response in MLRs between T cells and PBMCs from different individuals. Moreover, as discussed in more detail elsewhere herein, this reduction is observed to occur in a dose dependent manner. This shows that LSCs can be used as a therapy to inhibit host rejection of a transplant, and in addition, prevent or otherwise inhibit graft versus host disease following transplantation.

One skilled in the art would appreciate, based upon the disclosure provided herein, that the ability of LSCs to suppress an allogeneic T cell response is not limited to an MLR between T cells and PBMCs from disparate individuals, but rather, the LSCs can be exploited to include suppression of an MLR between T cells and any type of cell from a different individual, for example a neural stem cell (NSC), a liver cell, a cardiac cell, a chondrocyte, a kidney cell, an adipose cell and the like.

Accordingly, the present invention encompasses methods for reducing and/or eliminating an immune response to a transplant in a recipient by administering to the recipient of the transplant an amount of LSCs effective to reduce or inhibit host rejection of the transplant. Without wishing to be bound to any particular theory, the LSCs that are administered to the recipient of the transplant inhibit the activation and proliferation of the recipient's T cells.

I. Isolation and Culturing of LSCs

The LSCs useful in the methods of the present invention may be isolated using a variety of methods known to those skilled in the art. In a preferred method, an LSC is isolated from a mammalian subject, preferably a human subject.

Based upon the disclosure provided herein, LSCs can be obtained from any source, for example, from the tissue donor, the transplant recipient or an otherwise unrelated source (a different individual or species altogether). The LSCs may be autologous with respect to the T cells (obtained from the same host) or allogeneic with to the T cells. In the case where the LSCs are allogeneic, the LSCs may be autologous with respect to the transplant to which the T cells are responding to, or the LSCs may be obtained from an individual that is allogeneic with respect to both the source of the T cells and the source of the transplant to which the T cells are responding to. In addition, the LSCs may be xenogeneic to the T cells (obtained from an animal of a different species), for example rat LSCs may be used to suppress activation and proliferation of human T cells in MLRs.

In a further embodiment, LSCs used in the present invention can be isolated, from liver of any species of mammals, including but not limited to, a human, a mouse, a rat, an ape, a gibbon, a bovine, and the like. Preferably, the LSCs are isolated from a mouse or a rat. More preferably, the LSCs are isolated from a human.

Based upon the present disclosure, LSCs can be isolated and expanded in culture, i.e. in vitro, to obtain sufficient numbers of cells for the use in the methods described herein. For example, LSCs can be isolated from a human liver and cultured in complete medium (DMEM low glucose containing 4 mM L-glutamine, 10% FBS, and 1% Pennicillin/Streptomycin). However, the invention should in no way be construed to be limited to any one method of isolating and culturing LSCs. Rather, any method of isolating and culturing LSCs should be construed to be included in the present invention.

Any medium capable of supporting fibroblasts in cell culture may be used to culture LSCs. Media formulations that support the growth of fibroblasts include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), and the like. A preferred medium for culturing LSCs is DMEM.

Any medium capable of supporting LSCs in vitro may be used to culture the LSCs. Media formulations that can support the growth of LSCs include, but are not limited to, Dulbecco's Modified Eagle's Medium (DMEM), alpha modified Minimal Essential Medium (αMEM), and Roswell Park Memorial Institute Media 1640 (RPMI Media 1640) and the like. Typically, 0 to 20% Fetal Bovine Serum (FBS) or 1-20% horse serum is added to the above medium in order to support the growth of LSCs. However, a defined medium can also be used if the growth factors, cytokines, and hormones necessary for culturing LSCs are provided at appropriate concentrations in the growth medium. Media useful in the methods of the invention may contain one or more compounds of interest, including but not limited to antibiotics, mitogenic or differentiation compounds useful for the culturing of LSCs. The cells may be grown at temperatures between 27° C. to 40° C., preferably 31° C. to 37° C., and more preferably in a humidified incubator. The carbon dioxide content may be maintained between 2% to 10% and the oxygen content between 1% and 22%. However, the invention should in no way be construed to be limited to any one method of isolating and culturing LSCs. Rather, any method of isolating and culturing LSCs should be construed to be included in the present invention.

Additional non-limiting examples of media useful in the methods of the invention contain fetal serum of bovine or other species at a concentration at least 1% to about 30%, preferably at least about 5% to 15%, most preferably about 10%. Embryonic extract of chicken or other species can be present at a concentration of about 1% to 30%, preferably at least about 5% to 15%, most preferably about 10%.

Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml.

Following isolation, LSCs are incubated in culture medium in a culture apparatus for a period of time, or until the cells reach confluency, before passing the cells to another culture apparatus. Following the initial plating, the cells can be maintained in culture for a period of about 6 days to yield the Passage 0 (P0) population. The cells can be passaged for an indefinite number of times, each passage comprising culturing the cells for about 6-7 days, during which the cell doubling times can range between 3-5 days. The culturing apparatus can be of any culture apparatus commonly used in culturing cells in vitro. A preferred culture apparatus is a culture flask, and a more preferred culture apparatus is a T-225 culture flask.

LSCs can be cultured in stromal cell medium for a period of time or until the cells reach a certain level of confluence. Preferably, the level of confluence is greater than 70%. More preferably, the level of confluence is greater than 90%. A period of time can be any time suitable for the culture of cells in vitro. Stromal cell medium may be replaced during the culturing of the LSCs at any time. Preferably, the stromal cell medium is replaced every 3 to 4 days. LSCs are then harvested from the culture apparatus whereupon the LSCs can be used immediately or they can be cryopreserved and stored for use at a later time. LSCs may be harvested by trypsinization, EDTA treatment, or any other procedure used to harvest cells from a culture apparatus.

LSCs described herein may be cryopreserved according to routine procedures. Preferably, about one to ten million cells are cryopreserved in stromal cell medium containing 10%

DMSO in vapor phase of liquid $N_2$. Frozen cells can be thawed by swirling in a 37° C. bath, resuspended in fresh growth medium, and grown as usual.

II. Therapy

As encompassed in the present invention, LSCs are typically isolated from a human. If the cell of the present invention is to be transplanted into a human subject, it is preferable that the LSC be isolated from that same subject so as to provide for an autologous transplant. However, allogeneic transplants are also contemplated by the present invention.

Thus, in another aspect of the invention, the administered LSCs may be allogeneic with respect to the recipient. An allogeneic LSC cell can be isolated from a donor that is a different individual of the same species as the recipient. Following isolation, the cell is cultured using the methods disclosed herein to produce an allogeneic product. The invention also encompasses an LSC that is xenogeneic with respect to the recipient.

Another embodiment of present invention encompasses the route of administering LSCs to the recipient of the transplant. LSCs can be administered by a route which is suitable for the placement of the transplant, i.e. a biocompatible lattice or a donor tissue, organ or cell, to be transplanted. LSCs can be administered systemically, i.e., parenterally, by intravenous injection or can be targeted to a particular tissue or organ, such as bone marrow. LSCs can be administered via a subcutaneous implantation of cells or by injection of the cells into connective tissue, for example muscle.

LSCs can be suspended in an appropriate diluent, at a concentration of from about 0.01 to about $5 \times 10^6$ cells/ml. Suitable excipients for injection solutions are those that are biologically and physiologically compatible with the LSCs and with the recipient, such as buffered saline solution or other suitable excipients. The composition for administration can be formulated, produced and stored according to standard methods complying with proper sterility and stability.

The dosage of the LSCs varies within wide limits and may be adjusted to the individual requirements in each particular case. The number of cells used depends on the weight and condition of the recipient, the number and/or frequency of administrations, and other variables known to those of skill in the art.

Between about $10^5$ and about $10^{13}$ LSCs per 100 kg body weight can be administered to the individual. In some embodiments, between about $1.5 \times 10^6$ and about $1.5 \times 10^{12}$ cells are administered per 100 kg body weight. In some embodiments, between about $1 \times 10^9$ and about $5 \times 10^{11}$ cells are administered per 100 kg body weight. In some embodiments, between about $4 \times 10^9$ and about $2 \times 10^{11}$ cells are administered per 100 kg body weight. In some embodiments, between about $5 \times 10^8$ cells and about $1 \times 10^1$ cells are administered per 100 kg body weight.

III. Host Rejection

In another embodiment of the present invention, LSCs are administered to the recipient prior to, or contemporaneously with a transplant to reduce and/or eliminate host rejection of the transplant. While not wishing to be bound to any particular theory, LSCs can be used to condition a recipient's immune system to the transplant by administering LSCs to the recipient, prior to, or at the same time as transplantation of the transplant, in an amount effective to reduce, inhibit or eliminate an immune response against the transplant by the recipient's T cells. The LSCs affect the T cells of the recipient such that the T cell response is reduced, inhibited or eliminated when presented with the transplant. Thus, host rejection of the transplant may be avoided, or the severity thereof reduced, by administering LSCs to the recipient, prior to, or at the same time as transplantation.

In yet another embodiment, LSCs can be administered to the recipient of the transplant after the administration of the transplant. Further, the present invention comprises a method of treating a patient who is undergoing an adverse immune response to a transplant by administering LSCs to the patient in an amount effective to reduce, inhibit or eliminate the immune response to the transplant, also known as host rejection of the transplant.

The invention is based on the discovery that LSCs do not stimulate allogeneic T cell proliferation. As such, the invention encompasses using LSCs to suppress T cell proliferation in response to transplant of an exogenous organ, tissue or cells. The invention also includes a method of administering an LSC to a patient in an amount effective to reduce an immune response with respect to T cell proliferation.

One skilled in the art would appreciate, based upon the disclosure provided herein, that LSCs can be exploited to include suppression of T cell proliferation in response to any type of organ, tissue or cell transplanted into a mammal and obtained from a different individual. For example, T cell proliferation in response to a cell including, but not limited to a neural stem cell (NSC), a liver cell, a cardiac cell, a chondrocyte, a kidney cell, an adipose cell, and the like, can be suppressed using LSCs.

The present invention encompasses a method of reducing and/or eliminating an immune response to a transplant in a recipient by administering to the recipient of the transplant an amount of LSCs effective to reduce or inhibit host rejection of the transplant. Without wishing to be bound to any particular theory, the LSCs that are administered to the recipient of the transplant inhibit the activation and proliferation of the recipient's T cells.

The transplant includes a biocompatible lattice or a donor tissue, organ or cell, to be transplanted. An example of a transplant may include, but is not limited to stem cells, skin cells or tissue, bone marrow, neural stem cells, and solid organs such as heart, pancreas, kidney, lung and liver.

IV. Graft Versus Host Disease

In addition to methods to reduce and/or eliminate host rejection of the transplant, the present invention also provides a method of reducing and/or eliminating an immune response by a donor transplant against a recipient thereof (i.e. graft versus host reaction). Accordingly, the present invention encompasses a method of contacting a donor transplant, for example a biocompatible lattice or a donor tissue, organ or cell, with LSCs prior to transplantation of the transplant into a recipient. The LSCs serve to ameliorate, inhibit or reduce an adverse response by the donor transplant against the recipient.

The invention is based on the discovery that LSCs do not stimulate allogeneic T cell proliferation. Based on the disclosure presented herein, LSCs can suppress T cell proliferation in an MLR reaction. The invention also includes a method of administering an LSC to a mammal in an amount effective to reduce an immune response with respect to T cell proliferation.

As discussed elsewhere herein, LSCs can be obtained from any source, for example, from the tissue donor, the transplant recipient or an otherwise unrelated source (a different individual or species altogether) for the use of eliminating or reducing an unwanted immune response by a transplant against a recipient of the transplant. Accordingly, LSCs can be autologous, allogeneic or xenogeneic to the tissue donor, the transplant recipient or an otherwise unrelated source.

In an embodiment of the present invention, the transplant is exposed to LSCs prior to transplantation of the transplant into the recipient. In this situation, an immune response against the transplant caused by any alloreactive recipient cells would be suppressed by the LSCs present in the transplant. The LSCs are allogeneic to the recipient and may be derived from the donor or from a source other than the donor or recipient. In some cases, LSCs autologous to the recipient may be used to suppress an immune response against the transplant. In another case, the LSCs may be xenogeneic to the recipient, for example mouse or rat LSCs can be used to suppress an immune response in a human. However, it is preferable to use human LSCs in the present invention.

In another embodiment of the present invention, the donor transplant can be "preconditioned" or "pretreated" by treating the transplant prior to transplantation into the recipient in order to reduce the immunogenicity of the transplant against the recipient, thereby reducing and/or preventing graft versus host disease. The transplant can be contacted with cells or a tissue from the recipient prior to transplantation in order to activate T cells that may be associated with the transplant. Following the treatment of the transplant with cells or a tissue from the recipient, the cells or tissue may be removed from the transplant. The treated transplant is then further contacted with LSCs in order to reduce, inhibit or eliminate the activity of the T cells that were activated by the treatment of the cells or tissue from the recipient. Following this treatment of the transplant with LSCs, the LSCs may be removed from the transplant prior to transplantation into the recipient. However, some LSCs may adhere to the transplant, and therefore, may be introduced to the recipient with the transplant. In this situation, the LSCs introduced into the recipient can suppress an immune response against the recipient caused by any cell associated with the transplant. Without wishing to be bound to any particular theory, the treatment of the transplant with LSCs prior to transplantation of the transplant into the recipient serves to reduce, inhibit or eliminate the activity of the activated T cells, thereby preventing restimulation, or inducing hyporesponsiveness of the T cells to subsequent antigenic stimulation from a tissue and/or cells from the recipient. One skilled in the art would understand based upon the present disclosure, that preconditioning or pretreatment of the transplant prior to transplantation may reduce or eliminate the graft versus host response.

For example, in the context of bone marrow or peripheral blood stem cell (hematopoietic stem cell) transplantation, attack of the host by the graft can be reduced, inhibited or eliminated by preconditioning the donor marrow by using the pretreatment methods disclosed herein in order to reduce the immunogenicity of the graft against the recipient. As described elsewhere herein, a donor marrow can be pretreated with LSCs from any source, preferably with recipient LSCs in vitro prior to the transplantation of the donor marrow into the recipient. In a preferred embodiment, the donor marrow is first exposed to recipient tissue or cells and then treated with LSCs. Although not wishing to be bound to any particular theory, it is believed that the initial contact of the donor marrow with recipient tissue or cells function to activate the T cells in the donor marrow. Treatment of the donor marrow with the LSCs induces hyporesponsiveness or prevents restimulation of T cells to subsequent antigenic stimulation, thereby reducing, inhibiting or eliminating an adverse affect induced by the donor marrow on the recipient.

In an embodiment of the present invention, a transplant recipient suffering from graft versus host disease may be treated by administering LSCs to the recipient to reduce, inhibit or eliminate the severity thereof from the graft versus host disease where the LSCs are administered in an amount effective to reduce or eliminate graft versus host disease.

In this embodiment of the invention, preferably, the recipient's LSCs may be obtained from the recipient prior to the transplantation and may be stored and/or expanded in culture to provide a reserve of LSCs in sufficient amounts for treating an ongoing graft versus host reaction. However, as discussed elsewhere herein, LSCs can be obtained from any source, for example, from the tissue donor, the transplant recipient or an otherwise unrelated source (a different individual or species altogether).

V. Advantages of Using LSCs

Based upon the disclosure herein, it is envisioned that the LSCs of the present invention can be used in conjunction with current modes, for example the use of immunosuppressive drug therapy, for the treatment of host rejection to the donor tissue or graft versus host disease. An advantage of using LSCs in conjunction with immunosuppressive drugs in transplantation is that by using the methods of the present invention to ameliorate the severity of the immune response in a transplant recipient, the amount of immunosuppressive drug therapy used and/or the frequency of administration of immunosuppressive drug therapy can be reduced. A benefit of reducing the use of immunosuppressive drug therapy is the alleviation of general immune suppression and unwanted side effects associated with immunosuppressive drug therapy.

It is also contemplated that the cells of the present invention may be administered into a recipient as a "one-time" therapy for the treatment of host rejection of donor tissue or graft versus host disease. A one-time administration of LSCs into the recipient of the transplant eliminates the need for chronic immunosuppressive drug therapy. However, if desired, multiple administrations of LSCs may also be employed.

The invention described herein also encompasses a method of preventing or treating transplant rejection and/or graft versus host disease by administering LSCs in a prophylactic or therapeutically effective amount for the prevention, treatment or amelioration of host rejection of the transplant and/or graft versus host disease. Based upon the present disclosure, a therapeutic effective amount of LSCs is an amount that inhibits or decreases the number of activated T cells, when compared with the number of activated T cells in the absence of the administration of LSCs. In the situation of host rejection of the transplant, an effective amount of LSCs is an amount that inhibits or decreases the number of activated T cells in the recipient of the transplant when compared with the number of activated T cells in the recipient prior to administration of the LSCs. In the case of graft versus host disease, an effective amount of LSCs is an amount that inhibits or decreases the number of activated T cells present in the transplant.

An effective amount of LSCs can be determined by comparing the number of activated T cells in a recipient or in a transplant prior to the administration of LSCs thereto, with the number of activated T cells present in the recipient or transplant following the administration of LSCs thereto. A decrease, or the absence of an increase, in the number of activated T cells in the recipient of the transplant or in the transplant itself that is associated with the administration of LSCs thereto, indicates that the number of LSCs administered is a therapeutic effective amount of LSCs.

Genetic Modification

In yet another embodiment of the present invention, the LSCs can be used as a gene therapy vehicle for the expression of an exogenous gene in a mammal. The benefit of using LSCs as a vehicle for gene therapy over the presently used cells is based on the novel discovery that LSCs can survive for longer periods of time when compared with cells presently used in the art for gene therapy applications.

Unless otherwise stated, genetic manipulations are performed as described in Sambrook et al. (2001, Molecular Cloning: A Laboratory Manual, Cold Spring Harbor Laboratory, New York). The present invention encompasses genetically modified LSCs, which have been engineered to express an exogenous gene. The exogenous gene can, for example, be an exogenous version of an endogenous gene (for example, a wild type version of the same gene can be used to replace a defective allele comprising a mutation). The exogenous gene is usually but not necessarily covalently linked with (i.e., "fused with") one or more additional genes. Exemplary "additional" genes include a gene useful for "positive" selection to select cells that have incorporated the exogenous gene, and a gene useful for "negative" selection to select cells that have incorporated the exogenous gene into the same chromosomal locus as the endogenous gene or both.

The cells of the present invention can also be used to express a foreign protein or molecule for a therapeutic purpose or in a method of tracking their assimilation and/or differentiation in the recipient. Thus, the invention encompasses expression vectors and methods for the introduction of an isolated nucleic acid into LSCs with concomitant expression of the isolated nucleic acid in the LSCs. Methods for introducing and expressing DNA in a cell are well known to the skilled artisan and include those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The isolated nucleic acid can encode a molecule used to track the migration, assimilation, and survival of LSCs once they are introduced in the recipient. Proteins useful for tracking a cell include, but are not limited to, green fluorescent protein (GFP), any of the other fluorescent proteins (e.g., enhanced green, cyan, yellow, blue and red fluorescent proteins; Clontech, Palo Alto, Calif.), or other tag proteins (e.g., LacZ, FLAG-tag, Myc, $His_6$, and the like).

Tracking the migration and assimilation of an LSC of the present invention is not limited to the use of a detectable molecule expressed by a vector or virus. The migration and assimilation of a cell can also be assessed using a series of probes that facilitate localization of transplanted LSCs within a mammal. Tracking an LSC transplant may further be accomplished using antibodies or nucleic acid probes for cell-specific markers associated with LSCs.

An isolated nucleic acid may be introduced to an LSC using viral vectors (retrovirus, modified herpes viral, herpes-viral, adenovirus, adeno-associated virus, lentiviral, and the like) or by direct DNA transfection (lipofection, calcium phosphate transfection, DEAE-dextran, electroporation, and the like).

When the purpose of genetic modification of the cell is for the production of a biologically active substance, the substance will generally be one that is useful for the treatment of a given disorder. For example, it may be desired to genetically modify cells so that they secrete a certain growth factor product.

The cells of the present invention can be genetically modified by introducing an isolated nucleic acid into the cells, to produce a molecule such as a trophic factor, a growth factor, a cytokine, and the like, which is beneficial to culturing the cells. In addition, the genetically modified cells can provide an additional therapeutic effect to the patient when transplanted into a patient in need thereof.

Cells can also be modified to express a certain growth factor receptor (r) including, but not limited to, p75 low affinity NGFr, CNTFr, the trk family of neurotrophin receptors (trk, trkb, trkC), EGFr, FGFr, and amphiregulin receptors. Cells can be engineered to produce various neurotransmitters or their receptors such as serotonin, L-dopa, dopamine, norepinephrine, epinephrine, tachykinin, substance-P, endorphin, enkephalin, histamine, N-methyl D-aspartate, glycine, glutamate, GABA, ACh, and the like. Useful neurotransmitter-synthesizing genes include TH, dopa-decarboxylase (DDC), DBH, PNMT, GAD, tryptophan hydroxylase, ChAT, and histidine decarboxylase. Genes that encode various neuropeptides which may prove useful in the treatment of CNS disorders, include substance-P, neuropeptide-Y, enkephalin, vasopressin, VIP, glucagon, bombesin, cholecystokinin (CCK), somatostatin, calcitonin gene-related peptide, and the like.

The cells of the present invention can also be modified to express a cytokine. The cytokine is preferably, but not exclusively selected from the group consisting of IL-12, TNFα, IFNα, IFNβ, IFNγ, IL-7, IL-2, IL-6, IL-15, IL-21, and IL-23.

According to the present invention, gene constructs which comprise nucleotide sequences that encode heterologous proteins are introduced into the LSCs. That is, the cells are genetically altered to introduce a gene whose expression has therapeutic effect in the individual. According to some aspects of the invention, LSCs from the individual to be treated or from another individual, or from a non-human animal, may be genetically altered to replace a defective gene and/or to introduce a gene whose expression has therapeutic effect in the individual being treated.

In all cases in which a gene construct is transfected into a cell, the heterologous gene is operably linked to regulatory sequences required to achieve expression of the gene in the cell. Such regulatory sequences typically include a promoter and a polyadenylation signal.

The gene construct is preferably provided as an expression vector that includes the coding sequence for a heterologous protein operably linked to essential regulatory sequences such that when the vector is transfected into the cell, the coding sequence will be expressed by the cell. The coding sequence is operably linked to the regulatory elements necessary for expression of that sequence in the cells. The nucleotide sequence that encodes the protein may be cDNA, genomic DNA, synthesized DNA or a hybrid thereof or an RNA molecule such as mRNA.

The gene construct includes the nucleotide sequence encoding the beneficial protein operably linked to the regulatory elements and may remain present in the cell as a functioning cytoplasmic molecule, a functioning episomal molecule or it may integrate into the cell's chromosomal DNA. An isolated nucleic acid may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements for gene expression include: a promoter, an initiation codon, a stop codon, and a polyadenylation signal. It is preferred that these elements be operable in the cells of the present invention. Moreover, it is preferred that these elements be operably linked to the nucleotide sequence that encodes the protein such that the nucleotide sequence can be expressed in the cells and thus the protein can be produced. Initiation codons and stop codons are generally considered to be part of a nucleotide sequence that encodes the protein. However, it is preferred that these elements are functional in the cells. Similarly, promoters and polyadenylation signals used must be functional within the cells of the present invention. Examples of promoters useful to practice the present invention include but are not limited to promoters that are active in many cells such as the cytomegalovirus promoter, SV40 promoters and retroviral promoters. Other examples of promoters useful to practice the present invention include but are not limited to tissue-specific promoters, i.e. promoters that function in some tissues but not in others; also, promoters of genes normally expressed in the cells with or without specific or general enhancer sequences. In some embodiments, promoters are used which constitutively express genes in the cells with or without enhancer sequences. Enhancer sequences are provided in such embodiments when appropriate or desirable.

The cells of the present invention can be transfected using well known techniques readily available to those having ordinary skill in the art. An isolated nucleic acid may be introduced into the cells using standard methods where the cell expresses the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA with desired sequences into the cell. In some embodiments, recombinant retrovirus vectors are used to introduce DNA with desired sequences into the cells. In some embodiments, standard $CaPO_4$, DEAE dextran or lipid carrier mediated transfection techniques are employed to incorporate desired DNA into dividing cells. Standard antibiotic resistance selection techniques can be used to identify and select transfected cells. In other embodiments, DNA is introduced directly into cells by microinjection. Similarly, well-known electroporation or particle bombardment techniques can be used to introduce foreign DNA into the cells. A second gene is usually co-transfected or linked to the therapeutic gene. The second gene is frequently a selectable antibiotic-resistance gene. Transfected cells can be selected by growing the cells in an antibiotic that will kill cells that do not take up the selectable gene. In most cases where the two genes are unlinked and co-transfected, the cells that survive the antibiotic treatment have both genes in them and express both of them.

It should be understood that the methods described herein may be carried out in a number of ways and with various modifications and permutations thereof that are well known in the art. It may also be appreciated that any theories set forth as to modes of action or interactions between cell types should not be construed as limiting this invention in any manner, but are presented such that the methods of the invention can be more fully understood.

The following examples further illustrate aspects of the present invention. However, they are in no way a limitation of the teachings or disclosure of the present invention as set forth herein.

EXAMPLES

Example 1

Characterization of Liver Stromal Cells

Production of LSCs

Adult cadaveric human livers from different donors designated Hu027 and Hu029 were used. The liver was perfused via portal vein and hepatic artery with EGTA-containing buffer for 15 minutes and 0.06% collagenase (Sigma Chemical Company, St. Louis, Mo.) for 30 minutes at 34° C. The cells were then passed through 1000, 500, 250 and 150 μm filters. Viable cells were fractionated under 500×g with COBE cell processor (Gambro BCT, Lakewood, Colo.) using 2-step (9% and 17%; Hu027 and Hu029 cells) or 12.5% (H0107 cells) OptiPrep gradients (Axis-Shield PoC AS, Oslo, Norway). Cells were frozen in medium containing 80% Hypothermosol (Bio Life Solutions Inc, Binghamton, N.Y.), 10% human AB serum and 10% dimethylsulfoxide (Sigma) for storage in liquid nitrogen.

For culturing, the cyropreserved liver stromal cells were thawed and counted. The cultures were seeded at about $1.62 \times 10^6$ cells/cm$^2$ in complete medium (DMEM low glucose containing 4 mM L-glutamine, 10% FBS, and 1% Pennicillin/Streptomycin). The LSCs were cultured and used in experiments discussed more fully below. Methods known in the art were used to characterize the phenotype of LSCs with respect to BMSCs and fibroblast cell lines purchased from American Type Culture Collection (ATCC) as follows:

Flow Cytometry Analysis:

Briefly, cells were washed in PBS containing 5% FBS and blocked with immunoglobulin prior to staining with fluorochrome tagged antibodies. Background staining was determined by incubating cells with isotype-matched fluorochrome-labeled immunoglobulins. About fifty thousand events (cells) were used for analysis of the LSCs on a Becton Dickinson FACSCaliber flow cytometer using Cell Quest acquisition software. Results from the flow analysis are summarized in Table 1. A "NEG" designation in Table 1 indicates less than 0.01% positive staining. It was observed that the surface marker, CD14, distinguished LSCs from BMSCs and the fibroblast cell lines tested. In addition, CD133 was observed to be a marker which is present in lower concentration on LSCs relative to BMSCs, and therefore may be used as a marker to distinguish LSCs from BMSCs.

TABLE 1

Surface Anitgen Profile (% Positive Cells)

| | | Fibroblast Source | | | | | | BMSC | | | | |
|---|---|---|---|---|---|---|---|---|---|---|---|---|
| | | | | | | Connective | Liver | | 005 | 006 | 008 | 005 | 009 |
| Cluster of Differentiation | Cluster Distribution Passage # | Fetal P15 | Lung P8 | Skin P6 | Spleen P7 | Tissue P10 | HV-027 P3 | HV-029 P3 | (CE) P3 | (CE) P3 | (CE) P4 | (CW) P3 | (CW) P3 |
| CD3 | (T Cell) | 1.9 | 1.2 | 0.7 | 8.7 | 2.8 | 0.1 | 0.95 | 2.1 | 3.8 | 3.4 | 1.8 | 2.6 |
| CD11a | LFA-1 alpha | NEG | NEG | NEG | NEG | NEG | 0.55 | NEG | 1.3 | NEG | NEG | NEG | NEG |

TABLE 1-continued

Surface Anitgen Profile (% Positive Cells)

| | | Fibroblast Source | | | | | | | BMSC | | | | |
|---|---|---|---|---|---|---|---|---|---|---|---|---|---|
| | Cluster | | | | | Connective | Liver | | 005 | 006 | 008 | 005 | 009 |
| Cluster of Differentiation | Distribution | Fetal P15 | Lung P8 | Skin P6 | Spleen P7 | Tissue P10 | HV-027 P3 | HV-029 P3 | (CE) P3 | (CE) P3 | (CE) P4 | (CW) P3 | (CW) P3 |
| CD13 | APN | 91.6 | 93.3 | 98 | 57.2 | 82.1 | 94.2 | 95.4 | 86.7 | 81.5 | 91.8 | 93.7 | 96.5 |
| CD14 | LPS-r | NEG | NEG | NEG | NEG | NEG | 13.8 | 6.7 | NEG | NEG | NEG | NEG | NEG |
| CD19 | Pan B cell | NEG | NEG | NEG | NEG | NEG | NEG | NEG | NEG | NEG | NEG | NEG | NEG |
| CD29 | β-1 Integrin | 83.1 | 74.6 | 92 | 90.4 | 70.5 | 94.5 | 93.6 | 80.1 | 67.6 | 86.7 | 84.8 | 89.3 |
| CD31 | PECAM-1 | 0.8 | 0.5 | 0.5 | 0.8 | 0.1 | 0.9 | 0.6 | 2 | 0.5 | 1.3 | 0.9 | 0.1 |
| CD34 | Hemat. Stem cell | NEG | 0.1 | NEG | 2.9 | 1 | 0.5 | 6.4 | NEG | NEG | 0.5 | NEG | 0.3 |
| CD40 | Co-stimulation | NEG | NEG | NEG | NEG | NEG | NEG | NEG | NEG | NEG | 1.9 | NEG | NEG |
| CD44 | H-CAM | ND | 91.2 | 94.9 | 89.3 | 67.9 | 96.3 | 95.4 | 91.5 | 90.3 | 86.1 | 93.1 | 96.1 |
| CD45 | Pan Leukocyte | NEG | NEG | NEG | NEG | NEG | NEG | 0.1 | NEG | NEG | NEG | NEG | NEG |
| CD54 | ICAM-1 | 76.2 | 19.3 | 46 | 80.9 | 73.6 | 94 | 85.2 | 55.8 | 47 | 17.9 | 35.7 | 49.8 |
| CD80 | B7-1 | 4.7 | 1.9 | 1.6 | 7.6 | 3.9 | 0.3 | 1.8 | 2.8 | 3.9 | 6 | 2.1 | 2.5 |
| CD86 | B7-2 | NEG | NEG | NEG | NEG | NEG | NEG | NEG | NEG | NEG | NEG | NEG | NEG |
| CD90 | Thy-1 | 92.4 | 85.7 | 97.7 | 93.3 | 70 | 95.7 | 95.5 | 87.5 | 77 | 93.1 | 90.4 | 92.4 |
| CD105 | Endoglin | 26.8 | 31.5 | 67.1 | 80.7 | 42.8 | 89.5 | 90 | 62.5 | 55.5 | 58.5 | 64.7 | 43.5 |
| CD119 | INF-γ-r | 3.7 | 2 | 1.1 | 0.5 | 0.5 | 5.2 | 5.2 | 22.3 | 0.8 | NEG | 3.8 | 1.3 |
| CD120a | TNFR1 | NEG | NEG | NEG | NEG | NEG | NEG | NEG | NEG | NEG | NEG | NEG | NEG |
| CD123 | IL-3-r | NEG | NEG | 2.7 | NEG | 0.8 | 2.8 | 1.2 | NEG | 0.2 | 0.3 | 3.3 | NEG |
| CD132 | Common γ chain | NEG | NEG | NEG | NEG | 4.2 | NEG | 5.8 | NEG | NEG | NEG | NEG | NEG |
| CD133 | AC 133 | 11.2 | 5 | 4.5 | 38.6 | 18.3 | 4 | 7.6 | 20.2 | 17.9 | 27.4 | 22.7 | 35.5 |
| CD212 | IL-12-r | NEG | NEG | NEG | NEG | 1.6 | NEG | 1.2 | NEG | NEG | NEG | NEG | NEG |
| MHC Class I | | 93.5 | 70.4 | 95.5 | 91.8 | 90.9 | 96.8 | 92.9 | 88.5 | 76.1 | 93.5 | 89.4 | 92.6 |
| MHC Class II | | NEG | NEG | NEG | NEG | NEG | 0.1 | 0.2 | NEG | NEG | 0.1 | NEG | NEG |

Differentiation Assay for Liver Derived Stromal Cells:

Differentiation assays were performed on human BMSCs and human LSCs. The assays tested the adipogenic and/or osteogenic differentiation potential of the cells.

Adipogenic Assays:

Cells were plated at $2\times10^5$ cells/well in growth medium. At confluence, adipogenic differentiation was performed in three cycles of induction/maintenance medium. Maintenance media was DMEM supplemented with 10% FBS, 10 μg/mL insulin, and 1× antibiotic/antimycotic. Induction (differentiation) media was maintenance medium supplemented with $10^{-6}$ M dexamethasone, 0.5 mM methyl isobutyl xanthine and 200 uM indomethacin. Each cycle encompassed a three day culture with adipogenic induction media followed by a one day culture with adipogenic maintenance medium. After this, the cells were washed with PBS, fixed with 10% formalin, stained with Oil Red O, and counter-stained with hematoxylin to assess adipogenic differentiation.

Osteogenic Assays:

Cells were plated at $2\times10^5$ cells/well either in growth medium or differentiation media (DMEM containing 10% FBS, dexamethasone, beta-glycerophosphate and ascorbic acid-2-phosphate). Media for both control and differentiation wells were changed every 3-4 days for three weeks. After this, the cells were washed with PBS and fixed with 10% formalin. Osteogenic differentiation was measured by assessing alkaline phosphatase activity and using von Kossa stain for mineral deposits.

The results of the differentiation assays are depicted in Table 2.

TABLE 2

| Stromal Cells | Adipogenic Results | Alk Phos Results | Von Kossa Results |
|---|---|---|---|
| BMSCs (+control) | +for lipid formation | Strongly Positive | Strongly Positive |
| LSC #1 (HV-027) | No Evidence of Lipid Vacuole formation | Weakly Positive | Negative |
| LSC #2 (HV-029) | No Evidence of Lipid Vacuole formation | Negative | Negative |

It was observed that BMSCs differentiated into fat cells (adipocytes) and bone producing cells (osteoblasts) whereas LSCs did not differentiate into either lineage.

Example 2

Immunogenicity of Liver Stromal Cells

The experiments presented herein demonstrated that LSCs expressed novel immunological characteristics in vitro. For example, LSCs were found to be non-immunogenic when mixed with allogeneic T cells, as it was observed that LSCs when contacted with allogeneic T cells did not induce the T cells to proliferate as compared with the amount of proliferation of T cells when contacted with allogeneic PBMCs. Also, it was discovered that LSCs were immunosuppressive for alloreactive T cell responses. Similar immunological characteristics have been described for mesenchymal stem cells (MSCs) (Di Nicola et al., 2002 Blood 99:3838; Tse et al. 2003 Transplantation 75:389; Le Blanc et al. 2003 Scand. J. Immunol. 57:11), but not for the majority of fibroblast populations derived from different tissue sources.

The materials and methods used in the experiments presented in this Example are now described.

MLR Assays

The immunogenicity of LSCs were evaluated by mixed lymphocyte reaction (MLR) using T cells as responding cells and allogeneic PBMCs as stimulator cells. T cells were purified from leukopheresis packs (AllCells, LLC, Berkeley, Calif.; Poietics, Rockville, Md.) by negative selection using mouse monoclonal antibodies (Serotec, Raleigh, N.C.) specific for monocytes (CD14), B cells (CD19), MHC class II, and NK cells (CD56) to label non-T cells for removal using magnetic beads coated with monoclonal anti-mouse IgG antibody (Dynal Biotech, Inc, Lake Success, N.Y.). The remaining population of cells after depletion was typically greater than 85% CD3 positive by flow cytometry analysis. T cells were suspended in culture medium: Iscove's Modified Dulbecco's Medium (IMDM) supplemented with sodium pyruvate, non-essential amino acids, 2-mercaptoethanol, antibiotic/antimycotic, and 5% human AB serum (all supplements were obtained from Gibco, Carlsbad, Calif. except human AB serum which was obtained from PelFreez, Brown Deer, Wis.). T cells were seeded into microtiter wells ($2 \times 10^5$/well) in 96-well low evaporation flat-bottom plates (BD Falcon, Franklin Lakes, N.J.) with allogeneic stimulator cells. Stimulator cells were irradiated with 5000 rads gamma irradiation using a cesium source (Isomedix Gammator B, Parsippany, N.Y.) prior to being plated at the numbers necessary for the experiment (usually titrated decrementally from a high dose of $5 \times 10^4$ cells/well). Cultures were set up in triplicate wells per treatment. T cell proliferation to alloantigens was determined by pulsing the cultures with $^3$H-thymidine on the $6^{th}$ day of culture. The cells were harvested onto filtermats 16 hours later using a 96 well cell harvester (Skatron, Molecular Devices Corp, Sunnyvale, Calif.), and the cells on the filtermats were counted using a Microbeta scintillation counter (Perkin Elmer, Turku, Finland).

Immunogenicity Experiments

The one-way MLR assay was used to evaluate T cell proliferation to allogeneic LSCs. Briefly, T cells ($2 \times 10^5$/well) were cultured with irradiated (5000 rads gamma radiation) allogeneic LSCs, autologous PBMCs, or allogeneic PBMCs (30,000 cells/well) in 96 well microtiter culture plates. The LSCs were obtained from two different donors designated 027 and 029. T cells were purified from PBMCs obtained from four different donors designated 002, 004, 005, and 006. T cell enrichment was achieved by negative selection, using magnetic beads (Dynal, Inc) to remove non-T cells. Mouse monoclonal antibodies (mAbs) specific for macrophages/monocytes/dendritic cells (anti-CD14), B cells (anti-CD19), NK cells (anti-CD56), and MHC class II antigens (anti-DR) were used to label these cells. Magnetic particles coated with goat anti-mouse IgG antibody were used to pull the cells out in a magnetic field. The resulting cell population was typically greater than 90% T cells by flow cytometry analysis using fluoresceinated anti-CD3 mAb to detect T cells. Cell culture medium used was Iscove's Modified Dulbecco's Medium (IMDM) supplemented with 5% human AB serum, non-essential amino acids, sodium pyruvate, pen-strep/fungizone, and 2-mercaptoethanol. The cultures were incubated in a humidified atmosphere of 5% $CO_2$ at 37° C. for 6 days, pulsed with $^3$H-thymidine (1 µCi/well) for 16 hrs, and the cells were harvested on day 7 using an automated 96 well cell harvester. The incorporated radioactivity was determined by scintillation counting and the results are reported as counts per minute (cpm).

In order for a test cell to be deemed immunogenic, three requirements must be met:

1) the test cell must induce a T cell proliferative response that is at least 750 cpm above the autologous response;

2) the Stimulation Index (T+test cell cpm/T+autologous cell cpm) must be greater than or equal to 3.0; and 3) there must be a statistically significant difference between T+autologous PBMCs and T+test cells (P<0.05, Student's t test).

To rule out genetic factors (i.e., MHC similarities) as for the cause of non-responsiveness, each test cell was cultured with at least 2 (preferably 3) different T cell donors. If any of the donors produced a positive response as described above, the test population was considered immunogenic. Using these criteria, it was concluded that fibroblasts derived from skin, spleen, lung, connective tissue, and fetal material are immunogenic.

The results of MLR experiments using four different T cell donors as responders and LSCs as stimulators, demonstrate that LSCs are not immunogenic (FIG. 1). It was observed that the T cell response against LSCs derived from the two different donors was similar to the response against autologous PBMCs. It was also observed that the T cell response against LSCs was significantly less than the response to allogeneic PBMCs. LSCs did not stimulate a significant response from any of the four T cell donors as defined by the three criteria discussed above.

Suppression Experiments

LSCs were added to one-way MLR assays to determine whether they could suppress alloreactive T cell proliferation. Briefly, LSCs from two different donors (027 and 029) were irradiated (5000R) and added to one-way MLR cultures comprising purified T cells (responder cells) and irradiated allogeneic PBMCs (stimulator cells). Purification of T cells and culture conditions for the MLR are described elsewhere herein. Fibroblasts derived from connective tissue, fetal tissue, lung, skin and spleen, were also added to MLR cultures to determine their relative suppression properties. All of these primary cell lines were purchased from American Type Culture Collection (ATCC). BMSCs were tested for their suppressive property as well. LSCs, fibroblasts, and BMSCs, respectively, were added to MLR cultures between different combination of T cells and PBMCs at a dose of 30,000 cells/well. Results are shown as percent suppression of the base MLR response to which no fibroblasts/stromal cells were added. Each bar represents the mean suppression of four different MLR cultures by each cell type (except for lung fibroblasts for which the mean was calculated from three different MLR cultures). Suppression was determined by comparing the response containing the test cells to the control MLR according to the following formula:

Percent Suppression=[1−(cpm of MLR culture containing test cells/cpm control MLR culture)]× 100.

Figure 2:
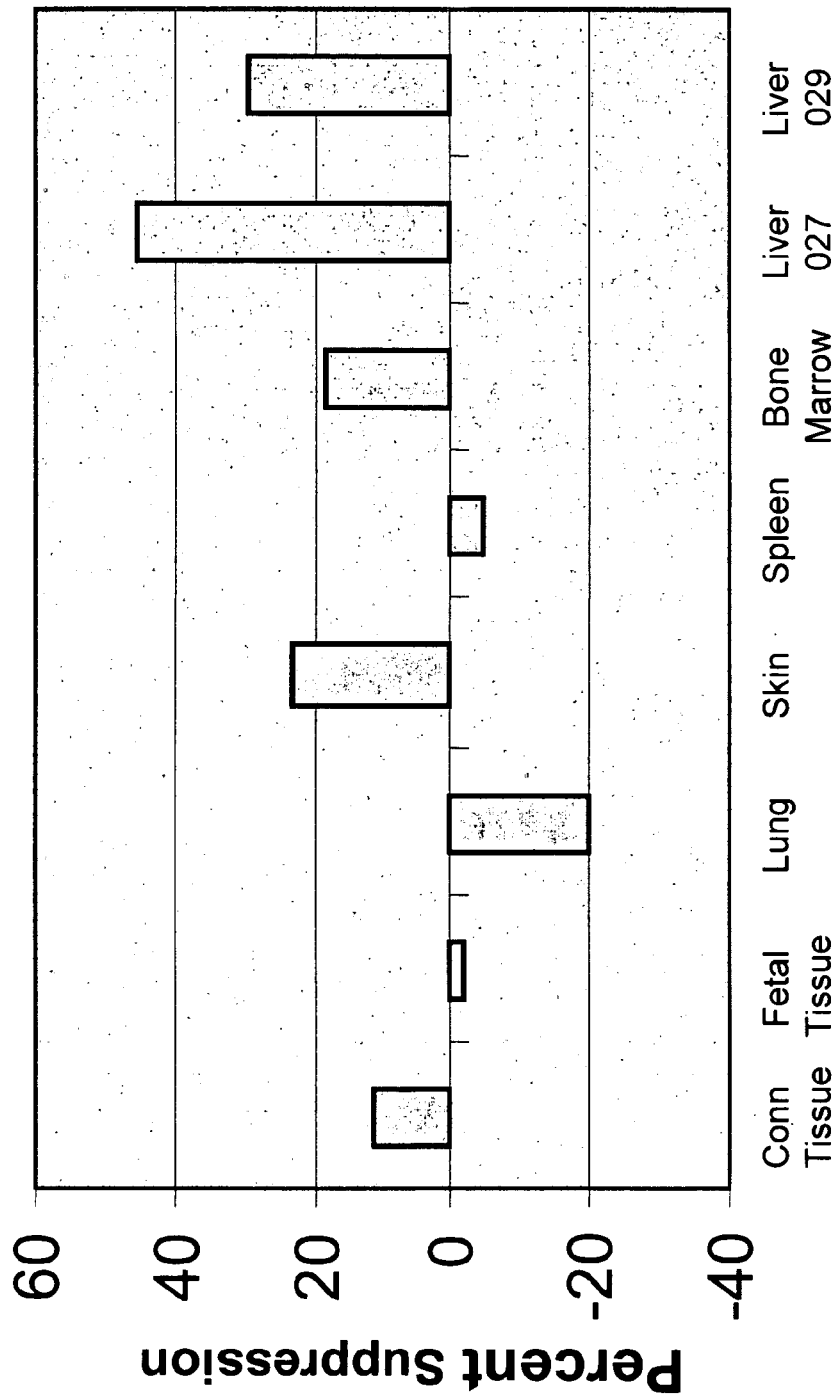
FIG. 2 is a graph depicting suppression of the (mixed lymphocyte reaction (MLR) response by fibroblast and stromal cells derived from various sources.

The results demonstrated that LSCs from both donors suppressed the MLR response to a greater extent than any other cell type that was evaluated (FIG. 2). The results shown are the averages of four experiments, each experiment using a different combination of T cells and PBMCs for the MLR. Connective tissue fibroblasts, skin fibroblasts, and bone marrow stromal cells were also observed to suppress the MLR response, whereas fetal fibroblasts, lung fibroblasts, and spleen fibroblasts enhanced the MLR response (negative 'Percent Suppression' indicates that the added test cell population enhanced the MLR response over control levels).

Example 3

Liver Stromal Cells in Transplantation

Given that LSCs suppress alloreactive T cell responses, as discussed elsewhere herein, LSCs can be co-transplanted with immunogenic cells, tissues, or organs to prevent immune rejection of the transplanted material. An advantage to this approach over those currently used in the art is that the cells can be used to establish restricted areas of immune privilege in the area of transplant without generalized suppression of the immune system which can be detrimental to the host.

The immunosuppressive properties of LSCs can be exploited to enhance the survival of transplanted cells, tissues, or organs. Without being bound to any particular theory, it is believed that LSCs delivered to a tissue/organ would create a localized area of immunosuppression or immune privilege which would aid in engraftment of cells, tissues, or organs. Although immune tolerance may be induced under these conditions, it is not required for the successful use of LSCs for the reduction and/or elimination of an immune response of effector cells against an alloantigen in a transplant recipient. It is preferred that there is a long-term engraftment of a sufficient number of LSCs at the desired site, wherein the LSCs maintain their suppressive phenotype.

The materials and methods used in the experiments presented in this Example are now described.

Isolation of LSCs:

As discussed elsewhere herein, LSCs were isolated from adult cadaveric human livers designated Hu027 and Hu029. Briefly, the liver was perfused via portal vein and hepatic artery and the cells were passed through 1000, 500, 250 and 150 μm filters. Viable cells were fractionated under 500×g with COBE cell processor (Gambro BCT, Lakewood, Colo.) using 2-step (9% and 17%; Hu027 and Hu029 cells) or 12.5% (H0107 cells) OptiPrep gradients (Axis-Shield PoCAS, Oslo, Norway).

Isolation and Culture of Human Fetal Neural Stem Cells:

Human fetal brain tissue can be purchased from Advanced Bioscience Resources (Alameda, Calif.). The tissue is washed with PBS/antibiotics and the meninges are removed prior to using the desired brain tissue. The remaining tissue is teased apart with a pair of forceps and further dissociated by trituration with a Pasteur pipette. Cells are then pelleted by centrifugation at 1000 rpm for 5 minutes at room temperature. The cell pellet is resuspended in 10 ml of NSC growth medium (DMEM/F12, 8 mM glucose, glutamine, 20 mM sodium bicarbonate, 15 mM HEPES, 8 μg/ml Heparin, N2 supplement, 10 ng/ml bFGF, 20 ng/ml EGF). The cells are plated on a coated (15 μg/ml Polyornithine overnight followed by 10 μg/ml human Fibronectin for greater than 4 h) T-25 $cm^2$ flask with vented cap and grown in a 5% $CO_2$ incubator at 37° C. Cells grown with Leukemia Inhibitory Factor (LIF) are plated in the complete growth medium with 10 ng/ml LIF after growing them initially (1-2 passages) in the presence of bFGF and EGF alone. Cultures are fed every other day by replacing 50% of the medium with fresh complete growth medium. Cells are passaged by trypsinization with 0.05% Trypsin-EDTA in PBS for 2-3 minutes followed by addition of soybean trypsin inhibitor to inactivate the trypsin. The cells are pelleted at 1200 rpm for 5 minutes at room temperature, resuspended in growth medium, and plated at $1.0-1.25 \times 10^5$ cells/$cm^2$ on coated flasks. Cells are cryopreserved in 10% DMSO+90% complete growth medium.

Human MLR Assays:

The immunogenicity of stem cells can be evaluated by mixed lymphocyte reaction (MLR) using T cells as responding cells and allogeneic PBMCs, NSCs, or LSCs as stimulator cells. If the stimulator cells are immunogenic to the T cells, the stimulator cells will activate the T cells and induce the T cells to proliferate. T cells used in these experiments are purified from leukopheresis packs as described elsewhere herein.

Rat MLR Assays:

These assays are set up in similar fashion to the human MLRs. Briefly, responder cells are produced by harvesting cervical plus mesenteric lymph node cells (LNCs). The responder cells are dissociated into a single-cell suspension by grinding them with a syringe plunger against a cell strainer (BD Falcon) in a 6-well plate. The responder cells are suspended in culture medium similar to human MLR medium with the exception that the serum is 10% FBS (HyClone, Logan, Utah). LNCs are seeded into microtiter wells ($4 \times 10^5$/well) with allogeneic stimulator cells at the numbers necessary for the experiment. Stimulator cells are irradiated (5000 rads) prior to being plated. Cultures are set up using triplicate wells per treatment. T cell proliferation to alloantigens are assessed as described elsewhere herein.

Human Alu PCR Assay:

The number of human NSCs in rat livers can be quantified using an intra-Alu element-based PCR assay described by Walker et al. (2003, Analytical Biochem. 315:122-128). The naturally occurring repetitive Alu sequence present in human DNA allows greater detection sensitivity over single copy sequences/genes. Thus, genomic DNA of human origin is quantified via RealTime PCR for the human-specific Alu repeat sequence. The primers employed for this assay amplify an intra-Alu core repeat sequence of ~200 bp within the Yb8 Alu subfamily. Use of these primers was reported by Walker et al. (2003, Analytical Biochem. 315:122-128) to allow human DNA specific detection to at least 10 pg (~1 cell equivalent) in 2 ng of mixed species sample DNA. Genomic DNA is isolated from snap-frozen rat livers using the Puregene DNA Isolation kit (Gentra Systems). Human DNA is quantitated by comparison with an Alu-specific DNA standard curve generated from populations of rat cells spiked (in 10-fold increments) with known numbers of human cells.

Co-Transplantation of LSCs with NSCs:

NSCs were chosen for the following experiments because NSCs represent an example of a stem cell that has significant clinical applications. However, it is envisioned that any cell, tissue or organ can be used in the following experiments. The following experiments address the role of LSCs in suppressing an immune response against NSCs transplanted into a recipient.

NSCs Express MHC Class I Antigens:

NSCs were prepared from human fetal tissue using methods well known in the art and were cultured for about 13 passages. The cells were evaluated for immunologically relevant cell membrane molecules using flow cytometry. It was observed that the population of NSCs did not express hematopoietic markers (CD45, CD14, CD34), costimulatory molecules (CD80, CD86), or MHC class II molecules. However, the NSCs did express the stem cell marker, CD133, as well as MHC class I antigens. The expression of class I molecules usually indicates that the cells would be recognized by alloreactive T cells and would be rejected if transplanted into an allogeneic recipient. Based on the disclosure presented herein, LSCs are an exception to this dogma because it was demonstrated that LSCs are not immunogenic to T cells in MLRs.

NSCs Stimulate Proliferation of Allogeneic T Cells

Figure 3:
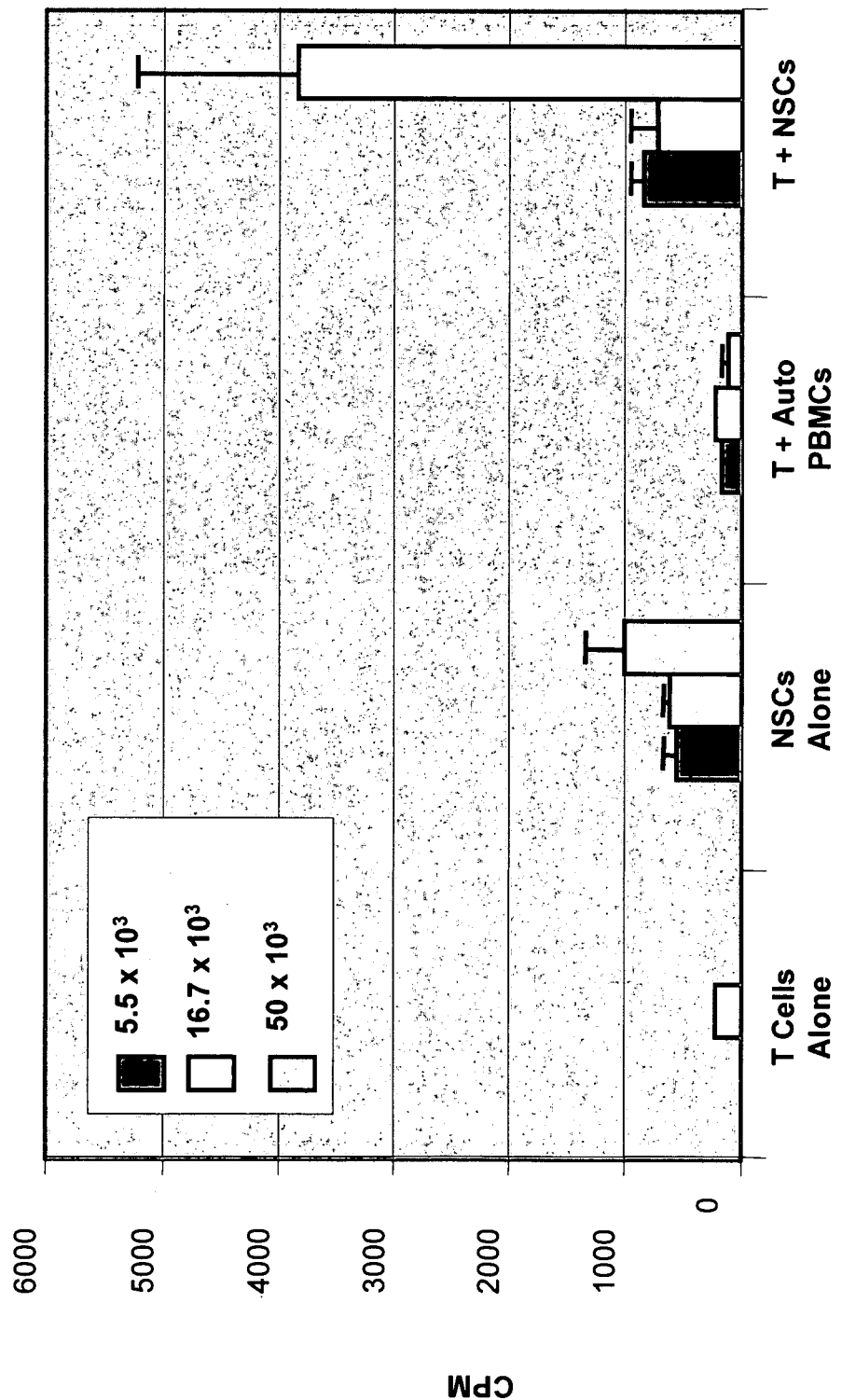
FIG. 3 is a graph demonstrating that neural stem cells (NSCs) stimulate proliferation of allogeneic T cells.

The immunogenicity of NSCs was evaluated by one-way mixed lymphocyte reaction (MLR) using T cells as responding cells and irradiated NSCs as stimulator cells. The MLR, which measures the T cell proliferative response to alloantigens, is predictive for survival of allogeneic cells in vivo. NSCs were prepared from human fetal tissue and cultured for about 13 passages. Starting with a high dose of about $5\times10^4$ cells/well, the cells were titrated down in 3-fold decrements as stimulator cells. Purified T cells ($2\times10^5$ cells/well) from an unrelated donor were prepared as responder cells. Autologous PBMCs were used as control stimulator cells. As shown in FIG. 3, NSCs stimulated a significant degree of T cell proliferation compared to autologous PBMCs, which did not stimulated a significant amount of T cell proliferation even at the highest cell dose ($P<0.05$, Student's t test). These results demonstrate that allogeneic NSCs are recognized by T cells and induce a functional immune response.

The ability of LSCs to protect NSCs from rejection in vivo can be examined using a xenogeneic model or an allogeneic model. Although the clinical model can involve xenogeneic transplantation of cells as well as an allogeneic model, a xenogeneic model is described herein to serve as proof of principle. The xenogeneic model encompasses the following criteria:

1) human NSCs as the donor cell;
2) rat LSCs because human LSCs have been shown to be suppressive for alloreactive T cell responses; and
3) the liver was chosen as the site of implantation due to the ease of administration of cells through the portal vein, the accessibility of the injected cells to the immune system, and the ability to recover injected cells. Without wishing to be bound to any particular theory, LSCs injected intraportally may become lodged in the liver. Further, since NSCs are approximately the same size as LSCs, NSCs may also become trapped in the liver after portal delivery. The use of human NSCs as the only human cell in this model enables the assessment of the engraftment using a PCR technique specific for human Alu DNA sequences. The model described herein also, can be used to determine whether the NSCs and LSCs induce a T cell response in the lymph nodes of recipient animals by using these cells in one-way MLR assays.

Suppression of Xenogeneic Rat Versus Human MLR by Rat LSCs

Xenogeneic MLRs can be set up between rat and human cells to evaluate whether rat LSCs can suppress this response. Rat LSCs allogeneic to the recipient are used in these experiments, but LSCs from any source can be used to suppress MLR responses. For example, rat LSCs autologous to the recipient can also be used.

Fisher rat lymph nodes (LNs) are harvested, dissociated into a single-cell suspension, and plated in microtiter wells ($4\times10^5$/well) as responder cells in the MLR. Human NSCs and allogeneic PBMCs are irradiated and plated at $1\times10^5$ cells per well as stimulator cells. LSCs and fibroblast from ACI strain rat are titrated into the MLRs at a high dose of $5\times10^4$ cells/well and 2-fold decremental doses down to 3,125 cells/well. Culture conditions for the rat MLR are as described elsewhere herein. Suppression is determined by comparing the control MLR (no LSCs) to MLRs containing fibroblasts or LSCs. Statistical evaluation are performed using the Student's t test.

Determine Survival of Transplanted NSCs

Experiments were designed to assess the survival of NSCs in vivo after administration with control fibroblasts or LSCs. 1:1 ratio of LSCs to NSCs can be used which should be adequate for suppression in vivo in view of a 1:3 ratio of LSCs to stimulator PBMCs being sufficient to suppress the MLR in vitro. Further, it is believed that PBMCs are stronger stimulators of T cells than NSCs, and therefore warranting the 1:1 ratio of LSCs to NSCs.

Human NSCs ($5\times10^6$ cells) are mixed with ACI strain rat dermal fibroblasts ($5\times10^6$ cells) and are injected intraportally in a volume of 200 µl into each of 25 Fisher rats. Dermal fibroblasts are produced from skin samples obtained from ACI rats and expanded using similar methods for expanding LSCs as described elsewhere herein. Another group of 25 Fisher rats are injected intraportally with human NSCs ($5\times10^6$ cells/rat) mixed with an equal number of ACI strain rat LSCs ($5\times10^6$ cells/rat). Five rats from each group are sacrificed on days 1, 7, 14, 21, and 28 after injection. The livers are removed, snap frozen, and subject to the Alu PCR assay as described elsewhere herein in order to assess the engraftment of the human NSCs.

It is believed that LSCs can mediate localized suppression in vivo, and extend the survival of xenogeneic cells in the liver. Thus, a greater numbers of human NSCs from rats that were given LSCs are recovered than from rats that received NSCs with non-suppressive fibroblasts. The greatest difference between these two groups would be expected to occur after 1-2 weeks, when the immune response is activated to the xenogeneic NSCs. A PCR assay can be used to detect human NSCs that have survived that transplantation by measuring the human-specific Alu repeat sequence.

Determine T Cell Priming to Injected Cells in Recipient Rats.

Experiments are designed to determine whether human NSCs co-transplanted with rat fibroblasts, or with rat LSCs primed reactive T cells in peripheral lymph nodes of recipient rats. A one-way MLR assay can be used to evaluate such priming.

Cervical and mesenteric lymph nodes (LNs) are removed from the two groups of 5 rats each (human NSCs+rat fibroblasts vs human NSCs+rat LSCs) which are sacrificed at the final time point, one month after injection. The LNs from the rats are dissociated into a single-cell suspension and used as responder cells in MLR assays with irradiated donor human NSCs; rat fibroblasts and rat LSCs are used as stimulator cells ($5\times10^4$ cells/well). Control groups used in these experiments can be irradiated syngeneic Fisher strain spleen cells as stimulators (background), LNCs cultured in medium alone, and irradiated stimulator cells cultured in medium alone. The mean response to each stimulator population are compared to background responses to syngeneic spleen cells.

Not wishing to be bound to any particular theory, in the event that xenogeneic human NSCs primed recipient rats, T cells from recipient rats should give a secondary response in the MLR assay to human NSCs as stimulator cells. In contrast, if LSCs administered to the recipient of the transplant prevented an immune response to the human NSCs following co-transplantation of the LSCs and human NSCs, recipient T cells should give a primary MLR response. If the transplanted LSCs tolerized recipient T cells to NSCs following co-transplantation of LSCs with NSCs, they should give reduced responses in an MLR.

Example 4

Co-Transplantation of LSCs with Islet Cells

LSCs can be used in co-transplantation with allogeneic islet cells for the treatment of diabetes. Allogeneic islets are introduced into a recipient by injecting islets with LSCs into the portal vein of the recipient which carries the cells to the liver, where the islets take up residence and function to produce insulin in response to glucose. While not wishing to be bound to any particular theory, co-transplantation of LSCs with allogeneic islet cells may function to protect the islets from rejection by the host without the use of immunosuppressive drugs. LSCs may also survive for extended periods of time in the liver since it is their tissue of origin.

It will be apparent to those skilled in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

What is claimed:

1. A method of reducing an immune response of effector cells against an alloantigen to the effector cells in a transplant recipient comprising: administering to the transplant recipient isolated adult liver stromal cells (LSCs) wherein the LSCs are incapable of differentiating into fat cells or bone producing cells, in an amount effective to reduce an immune response of effector cells against an alloantigen to the effector cells, whereby in the transplant recipient the effector cells have a reduced immune response against the alloantigen.

2. The method of claim 1, wherein said effector cells are T cells.

3. The method of claim 2, wherein said T cells are from a donor and the alloantigen is from said recipient.

4. The method of claim 2, wherein said T cells are from said recipient and the alloantigen is from a donor.

5. The method of claim 2, wherein said T cells are present in a transplant.

6. The method of claim 1, wherein the transplant recipient receives a bone marrow transplant.

7. The method of claim 1, wherein the transplant recipient receives a hematopoietic stem cell transplant.

8. The method of claim 1, wherein the transplant recipient receives a neural stem cell transplant.

9. The method of claim 1, wherein prior to said administering to a transplant recipient liver stromal cells, said liver stromal cells have been expanded in culture.

10. The method of claim 1, wherein said effector cells are T cells from a donor previously activated by contacting said T cells with a cell or a tissue from the recipient prior to transplantation in order to activate said T cells, and further wherein said immune response is the reactivation of said T cells.

11. The method of claim 1, wherein the liver stromal cells are administered to the transplant recipient to treat rejection of the transplant by the recipient.

12. The method of claim 1, wherein the liver stromal cells are human liver stromal cells.

13. The method of claim 1, further comprising administering to the recipient an immunosuppressive agent.

14. The method of claim 1, wherein the transplant is a solid organ.

15. The method of claim 14 wherein the solid organ is selected from the group consisting of heart, pancreas, kidney, lung and liver.

16. The method of claim 1, wherein said liver stromal cells are administered to the recipient prior to a transplant.

17. The method of claim 1, wherein said liver stromal stem cells are administered to the recipient concurrently with a transplant.

18. The method of claim 17, wherein said liver stromal cells are administered as part of a transplant.

19. The method of claim 1, wherein the liver stromal cells are administered to the recipient subsequent to the transplantation of a transplant.

20. The method of claim 1, wherein said liver stromal cells are administered intravenously to the recipient.

21. The method of claim 1, wherein said effector cells are cells of a recipient of a donor transplant.

22. The method of claim 1, wherein said liver stromal cells are genetically modified.

23. A method for reducing an immune response of effector cells against an alloantigen to the effector cells in a transplant recipient comprising:
    administering to a recipient a transplant treated with isolated adult liver stromal cells (LSCs) wherein the LSCs are incapable of differentiating into fat cells or bone producing cells in an amount effective to reduce an immune response of effector cells against an alloantigen to the effector cells, whereby in the transplant recipient the effector cells have a reduced immune response against the alloantigen.

24. The method of claim 23 wherein said effector cells are T cells.

25. A method of reducing an immune response of effector cells against allogeneic cells, the method comprising treating the effector cells with isolated adult liver stromal cells, (LSCs), wherein the LSCs are incapable of differentiating into fat cells or bone producing cells.

26. The method of claim 25 wherein said effector cells are T cells.

* * * * *